US008345253B2

(12) United States Patent
Malic et al.

(10) Patent No.: US 8,345,253 B2
(45) Date of Patent: Jan. 1, 2013

(54) SYSTEM AND METHOD FOR SURFACE PLASMON RESONANCE BASED DETECTION OF MOLECULES

(75) Inventors: Lidija Malic, Montreal (CA); Maryam Tabrizian, Longueuil (CA); Teodor Veres, Montreal (CA); Bo Cui, Boucherville (CA); Francois Normandin, Montreal (CA)

(73) Assignee: The Royal Institution for the Advancement of Learning/McGill University and Her Majesty the Queen in Right of Canada, Montreal, Boucherville (CA)

( * ) Notice: Subject to any disclaimer, the term of this patent is extended or adjusted under 35 U.S.C. 154(b) by 0 days.

(21) Appl. No.: 12/527,961

(22) PCT Filed: Feb. 21, 2008

(86) PCT No.: PCT/CA2008/000342
§ 371 (c)(1),
(2), (4) Date: Aug. 20, 2009

(87) PCT Pub. No.: WO2008/101348
PCT Pub. Date: Aug. 28, 2008

(65) Prior Publication Data
US 2010/0045995 A1 Feb. 25, 2010

Related U.S. Application Data

(60) Provisional application No. 60/890,863, filed on Feb. 21, 2007.

(51) Int. Cl.
*G01N 21/55* (2006.01)

(52) U.S. Cl. ........ 356/445; 356/246; 204/450; 436/180; 436/150; 506/9

(58) Field of Classification Search .................. 356/445, 356/246; 436/150, 180; 435/6
See application file for complete search history.

(56) References Cited

U.S. PATENT DOCUMENTS

| 6,958,132 | B2 | 10/2005 | Chiou et al. | |
| 6,989,234 | B2* | 1/2006 | Kolar et al. | ........................ 435/6 |
| 7,048,889 | B2* | 5/2006 | Arney et al. | .................. 422/68.1 |
| 7,439,014 | B2* | 10/2008 | Pamula et al. | ..................... 435/4 |
| 2003/0036206 | A1* | 2/2003 | Chien et al. | ................... 436/180 |
| 2003/0124623 | A1 | 7/2003 | Yager et al. | |
| 2004/0231987 | A1* | 11/2004 | Sterling et al. | ................ 204/450 |
| 2006/0146099 | A1 | 7/2006 | Wang et al. | |
| 2006/0194331 | A1 | 8/2006 | Pamula et al. | |

FOREIGN PATENT DOCUMENTS

WO 2005019875 3/2005

* cited by examiner

*Primary Examiner* — Tarifur Chowdhury
*Assistant Examiner* — Isiaka Akanbi
(74) *Attorney, Agent, or Firm* — Perley-Robertson, Hill & McDougall LLP

(57) ABSTRACT

A system and method for molecule detection uses a surface plasmon resonance (SPR) system with detection spots having fixed nanostructures. An SPR assembly may be combined with a digital microfluidic control system such as an electrowetting-on-dielectric (EWOD) chip. The microfluidic system individually directs sample droplets to different detection spots of the SPR assembly, thus allowing the SPR examination of different samples or sample reactions on the same surface. The nanostructures at the detection spots enhance the sensitivity of the SPR signals.

21 Claims, 5 Drawing Sheets

SYSTEM AND METHOD FOR SURFACE PLASMON RESONANCE BASED DETECTION OF MOLECULES

FIELD OF THE INVENTION

The invention relates generally to the detection of molecules such as DNA, proteins and the likes, and more specifically to the detection of molecules using Surface Plasmon Resonance (SPR).

BACKGROUND OF THE INVENTION

Currently employed molecular biology laboratory protocols are laborious, throughput-limited and suffer from low sensitivity and specificity for low analyte concentration detection. Proteomic and nucleic acid array technology itself has revolutionized the practice of life sciences research, providing quantitative information on complex biological systems in a fraction of the time required by traditional methods. However, the application of such technology for quantitative measurement of biomolecules has been limited by the high costs and laborious techniques associated with radioactive and fluorescent labeling and detection. In addition, such assays also pose additional problems associated with the use and disposal of radioactive labels.

In traditional assays, the protein or DNA arrays are flooded with a solution containing labeled target biomolecules, incubated overnight, rinsed, and then "read-out" using fluorescence detection methods. This is not only time-consuming, but still requires large sample concentrations. On the other hand, direct, label-free detection techniques, such as surface plasmon resonance exhibit lower sensitivity and throughput, thus making them unsuitable for detection of very low concentrations of the target analyte. Hence, there is a need for a platform that would provide increased sensitivity and specificity (for low concentration detection) and increased throughput (parallel detection), and would allow a direct detection technique that has a small amount of analyte consumption and short assay time, while still being low in cost.

SUMMARY OF THE INVENTION

In accordance with the present invention, a sample support apparatus is provided for fluid samples introduced to a multichannel surface plasmon resonance (SPR) detector. The support apparatus includes an SPR assembly having a metal electrode in electrical contact with a plurality of metal detection spots. Adjacent to each of the detection spots, a droplet of the fluid samples may be secured for subsequent SPR detection. To position the fluid droplets relative to the detection spots, a microfluidic control system is used by which the droplets may be selectively displaced and positioned relative to the detection spots. In this way, each droplet may be individually conducted to a desired detection spot independent of other fluid droplets, such that sample droplets with different sample materials may be simultaneously located at different respective detection spots.

In one embodiment of the invention, the microfluidic control system makes use of an electrowetting-on-dielectric (EWOD) structure. This may be in the form of a plate in which are embedded a plurality of control electrodes. The SPR assembly may also be in the form of a plate, with each of the detection spots having a different location on the plate surface. The two plates may be positioned adjacent to each other with a space between them within which the fluid droplets reside. The surfaces of the two plates that contact the droplets may have a hydrophobic coating, with the exception of the detection spots.

In one aspect of the invention, an SPR sample support apparatus is provided that has an electrode connected to detection spots that each includes a plurality of nanostructures. The nanostructures may be of different shapes, such as nano-pillars, nano-posts, non-spots, nano-dots, nano-particles, nano-brushes or nano-prisms. Various materials may also be used, such as gold, silver or carbon, and the nanostructures may be decorated with quantum dots. The nanostructures and provide an enhanced SPR signal for samples adjacent thereto. In one particular embodiment, the nanostructure material is gold, as is the electrode. The nanostructure detection spots are fixed to the support, providing a predictable and reproducible effect on the SPR signal for an adjacent sample material.

The nanostructure detection spots may also be used with the sample support apparatus having an SPR assembly and a microfluidic control system. The combination of the two, as discussed above, allows for the dynamic addressing of different detection spots for individual fluid sample droplets. The use of nanostructures for these detection spots provides for an enhancement of the SPR signal of the sample material. Moreover, the nanostructures provide a degree of hydrophobicity for the detection spots.

BRIEF DESCRIPTION OF THE DRAWINGS

Further features and advantages of the present invention will become apparent from the following detailed description, taken in combination with the appended drawings, in which.

DETAILED DESCRIPTION OF THE INVENTION

In an exemplary embodiment of the invention, there is provided a system for the detection of molecules and for measuring molecular interactions, the system comprising a microfluidic sample support optically coupled to a Surface Plasmon Resonance (SPR) multi-channel detection system (such as an SPR imaging system). The microfluidic sample support is adapted for providing a plurality of dynamically-addressable and reconfigurable sample domains thereby enabling highly flexible multiplexed SPR detection.

Figure 1:
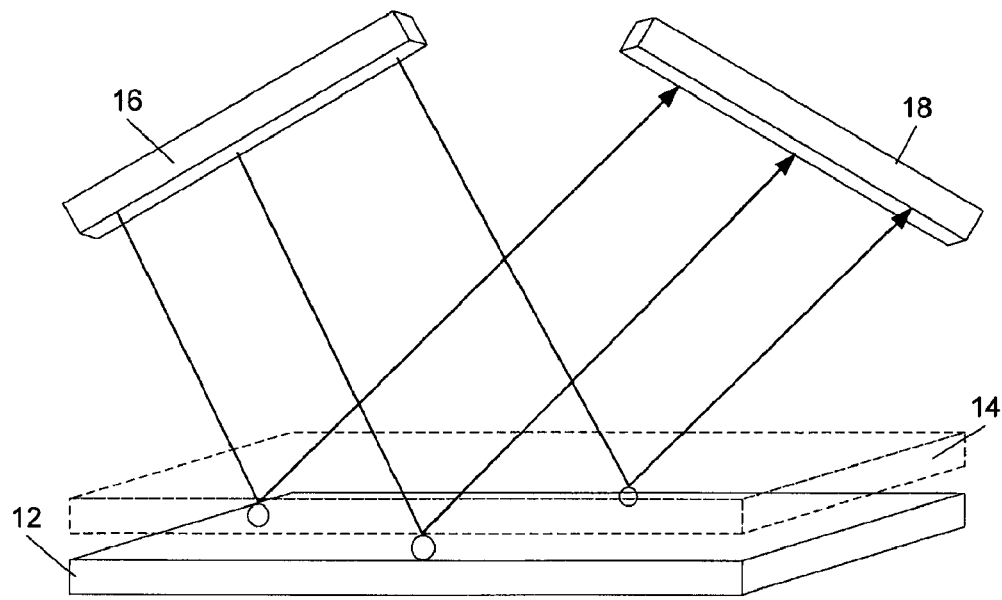
FIG. 1 is a schematic perspective view of an integrated microfluidic-based SPR sample support according to the present invention.

The basic structure of this embodiment is shown in FIG. 1. A microfluidic sample support includes two plates, between which a fluid containing the molecules of interest resides. A microfluidic plate 12 makes use of a known microfluidic technology that can be used to selectively displace droplets of the fluid, thereby enabling them to be positioned at desired locations (domains). Examples of such microfluidic technologies include, but are not limited to, optical droplet manipulation, opto-electrowetting and electrowetting on dielectric (EWOD). Some examples are shown in U.S. Pat. Nos. 6,734,436 and 6,958,132, as well as in U.S. Patent Application Publication Nos. US2005/056569, US2006/0146099 and US2006/0194331. The second plate 14 has a substrate that allows a fluid between the plates to be optically coupled to an SPR detection system and that, together with the plate 12, can immobilize the droplets. Also shown schematically in the figure are an SPR beam source 16 and a CCD array 18 for detection of the SPR signal, although those skilled in the art will understand that this is a simplified representation, and that the SPR system is more complex than shown.

Figure 2:
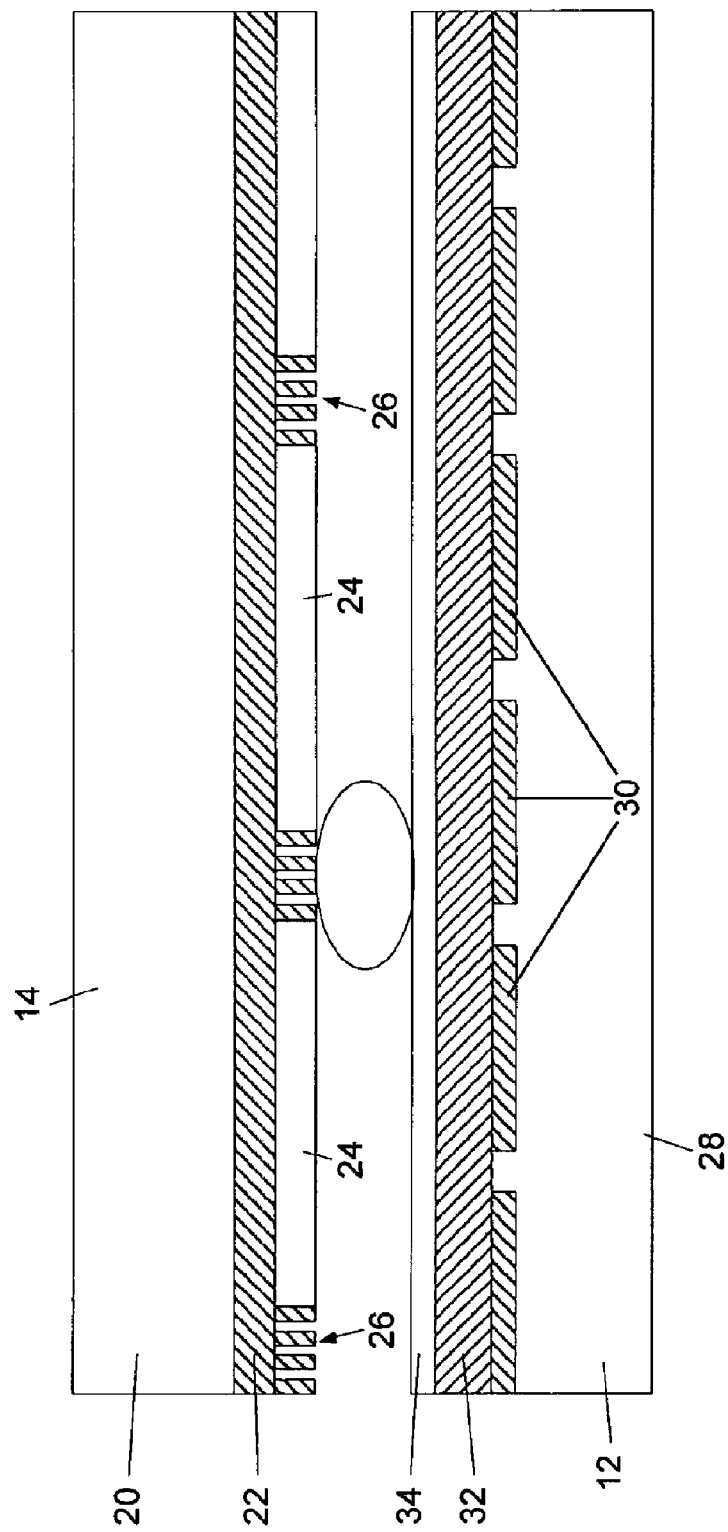
FIG. 2 is a schematic cross-sectional view of a sample support that may be used in the configuration of FIG. 1.

A more specific illustration of the exemplary embodiment is shown in FIG. 2. Top plate 14 includes a glass or plastic substrate 20 that is transparent to SPR signals and a ground electrode 22, which is a conductive material such as gold. Adjacent to the ground electrode 22 is a hydrophobic coating 24 interspersed with detection spots 26. In this embodiment, the detection spots are each made up of a group of conductive nanostructures. It is possible to have such detection spots without nanopatterning, but the nanostructures provide certain advantages, as discussed below. The detection spots 26 are in conductive contact with the ground electrode 22, and are patterned in this embodiment using electron beam or nano-imprint lithography to form pillar-shaped nanostructures. The nanopatterning of the detection spots enhances both the wettability of the surface (via large contact angle), as well as the surface plasmon resonance condition.

Also shown in FIG. 2 is bottom plate 12, which includes a glass substrate 28 in which are embedded a series of control electrodes 30. Adjacent the control electrodes 30 is an insulating layer 32 which, in turn, is covered by a hydrophobic coating 34 that separates the insulating layer from the sample fluid droplets. The control electrodes are organized in a two-dimensional array in the bottom plate, and electrical potentials may be selectively placed at certain control electrodes so as to move a sample droplet to a desired location relative to the plate surface. An example of droplet movement relative to the location of detection spots on the top plate 14 is shown schematically in FIG. 3.

Figure 3:
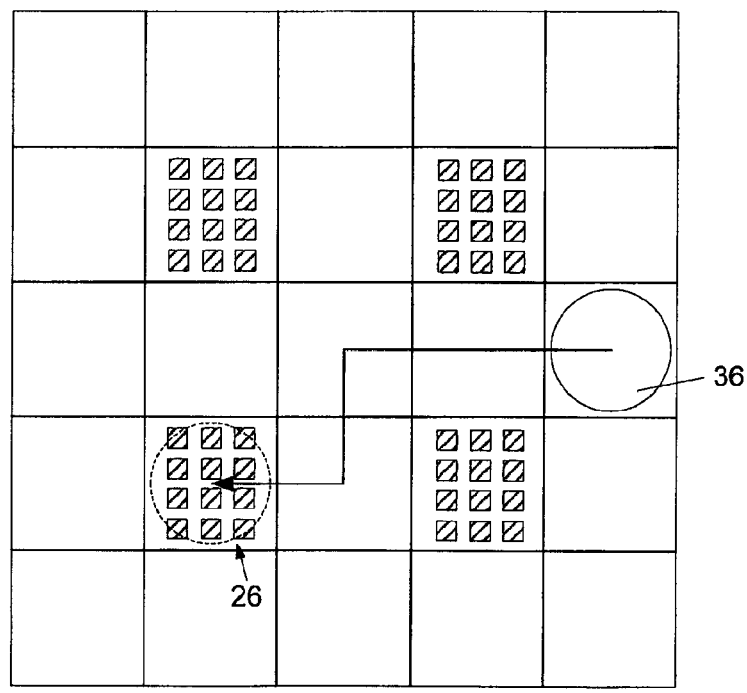
FIG. 3 is a schematic depiction of fluid sample droplet transport using the sample support of FIG. 2.

Using charges placed on certain electrodes, a droplet 36 may be moved along the surface of the plate and positioned adjacent to a desired detection spot 26. As shown in the example of FIG. 3, the droplet 36 is moved from its original position along a path indicated by the arrow in the figure, until finally arriving at the desired location. This type of microfluidic control is known generally within the field of electrowetting-on-dielectric (EWOD) type devices, and is discussed in more detail below. However, implementation of EWOD droplet control in the present invention allows different droplets to be selectively positioned at different desired detection spots. Once a droplet is positioned adjacent to one of the detection spots 26, an SPR signal is enhanced by the presence of the nanostructures at the detection spot.

Figure 4:
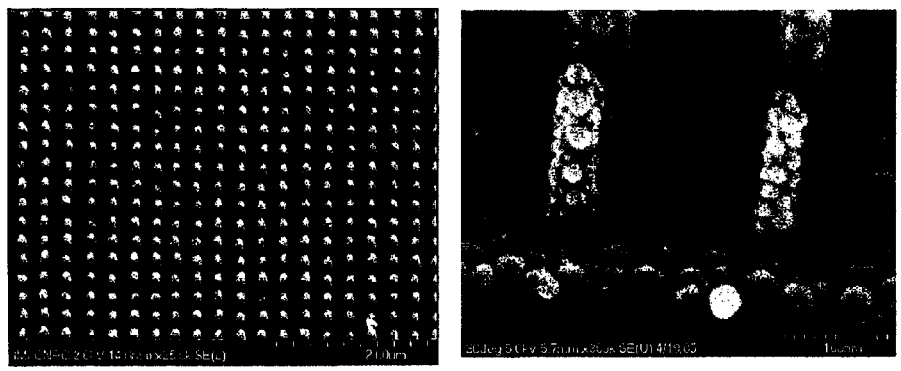
FIG. 4 shows scanning electron microscope (SEM) images of pillar nanostructures used for SPR signal enhancement in the present invention.

The nanopatterning of the sensing surface according to the present invention may be accomplished, for example, using nano imprint or e-beam lithography to create different nanostructures on the glass or plastic substrate. The sensitivity enhancement comes from two areas provided by the nanostructures: (i) the increase in the available surface area for the immobilization of a sample (such as a DNA probe); and (ii) the enhancement of the electromagnetic field at the interface resulting in a larger angular shift of the SPR spectrum dip. An example of nanostructures that may be used in a glass substrate is depicted in FIG. 4, which shows scanning electron microscope images of pillar nanostructures at two different resolutions. Besides creating LSP-SP interactions that enhance the SPR signal, utilization of nanostructures significantly increases the area of the reaction surface (2D vs. flat 1D surface) allowing for more binding sites and further increase in the detection signal.

In the present embodiment, incorporation of the nanostructures is done by modification of the top plate. The nanopatterning of the electrode surface by means of different nanostructures enhances both the wettability of the surface (which favors the biomolecules adsorption on the surface) and the surface plasmon resonance condition to deliver an increase in the sensitivity of the measurement. Advantageously, the nanostructures also facilitate the droplet movement, so that there is no need for coating the gold surface with a hydrophobic polymer.

An exemplary application of the invention is the sensitive, real-time detection of DNA hybridization on a microarray platform. In one embodiment, an electrowetting-on-dielectric (EWOD) biochip with appropriate surface modification for optimal binding capacity and specificity can be coupled with surface plasmon resonance imaging to meet the requirements for microarray DNA hybridization detection technology. The microfluidic sample support may be an EWOD actuation technology where droplets containing a sample (or target molecules) are displaced on the support such as to dynamically position the sample at specific locations (or "domains") on the surface of the chip. The motion of the droplet is achieved by voltage applied to a specific grid point. Such a system provides for lower analyte consumption and reduced assay time.

In this embodiment, the bottom plate is the control plate and contains an array of independently addressable electrodes embedded in an insulating dielectric layer. In one possible construction, each electrode is individually connected to a solder pad along two opposite edges of the substrate, and the connections are established using soldering to connect switches to the electrode-connected pads. Optionally, an electronic test clip can be used to connect the chip contact pads. A computer-controlled electronic interface can be used to switch the outputs to which a DC or AC voltage (preferably from a high-power voltage source) is applied to energize a particular electrode (or set of electrodes). In general, standard EWOD control technology may be used with the invention, and will therefore not be discussed in any great detail herein.

In one particular embodiment, optimization of electrode configuration and the required dielectric film thickness can be accomplished by the simulation and modeling of EWOD droplet actuation using multi-physics simulation software Flow 3D (Flow Science Inc., Santa Fe, N. Mex., USA). Based on the optimum electrodes configuration, their respective geometry and required separation to achieve the desired droplet actuation pathway, photolithographic masks can be designed using AutoCAD software.

The construction of the support plate uses certain known materials and processes. The bottom plate may be fabricated on glass, plastic or a silicon wafer. The hydrophobic coating can be deposited on both plates as the finishing surface to facilitate droplet motion. Furthermore the hydrophobic coating, when present, can be patterned so as to expose specific areas of the electrode and to provide "domains" in which the sample will be immobilized by adsorption of the electrode surface. In one example, the fabrication of the bottom plate starts with a clean glass substrate, onto which 100 nm thick Chromium layer is deposited using e-beam evaporation or sputtering and patterned photolithographically to define the electrode patterns. Alternatively, ITO, Al, Au, Cu, Pt may also be used for the metal electrodes. Next, a film of $SiO_2$ or SiN is conformally deposited by sputtering to a thickness of 100 nm to 1 µm. Optionally, SU-8 can be spin-coated to a thickness of 1-5 µm to serve as a dielectric layer. On top of this film a very thin (15-20 nm) amorphous fluoropolymer layer (e.g., Teflon AF 1600) is spin-coated to make the surface hydrophobic.

The top plate, which functions as the SPR biochip, contains the ground electrode adjacent to which the sample is to be immobilized. This is deposited on a transparent substrate, as is needed for the SPR detection technique. In one example, the fabrication of the top plate starts with a pre-cleaned glass or plastic substrate onto which a ground electrode is electron-beam evaporated. In this example, the ground electrode is a gold film with a thickness of 40 nm, although a different noble metal (e.g., silver) may also be used. An adhesion promoter, such as a 1 nm Cr film, can be used between the electrode and the substrate. Next, a positive resist is spin-coated and patterned using photolithography (UV exposure under mask) to define the detection surface pattern by selectively protecting this area from the subsequent hydrophobic coating deposition. A thin layer (e.g., 20 nm) of the coating is deposited, a possible material being an amorphous fluoropolymer, such as TEFLON AF1600 (TEFLON is a registered trademark of E.I. DuPont de Nemours and Co., Wilmington, Del.). Self-assembled hydrophobic thiols may also be used as a hydrophobic film. With a subsequent photoresist lift-off in acetone, the fluoropolymer layer sitting on top of this photoresist is also removed, and the resulting detection surface consists of spots of bare gold onto which samples such as ss-DNA probe can be immobilized.

Figure 5:
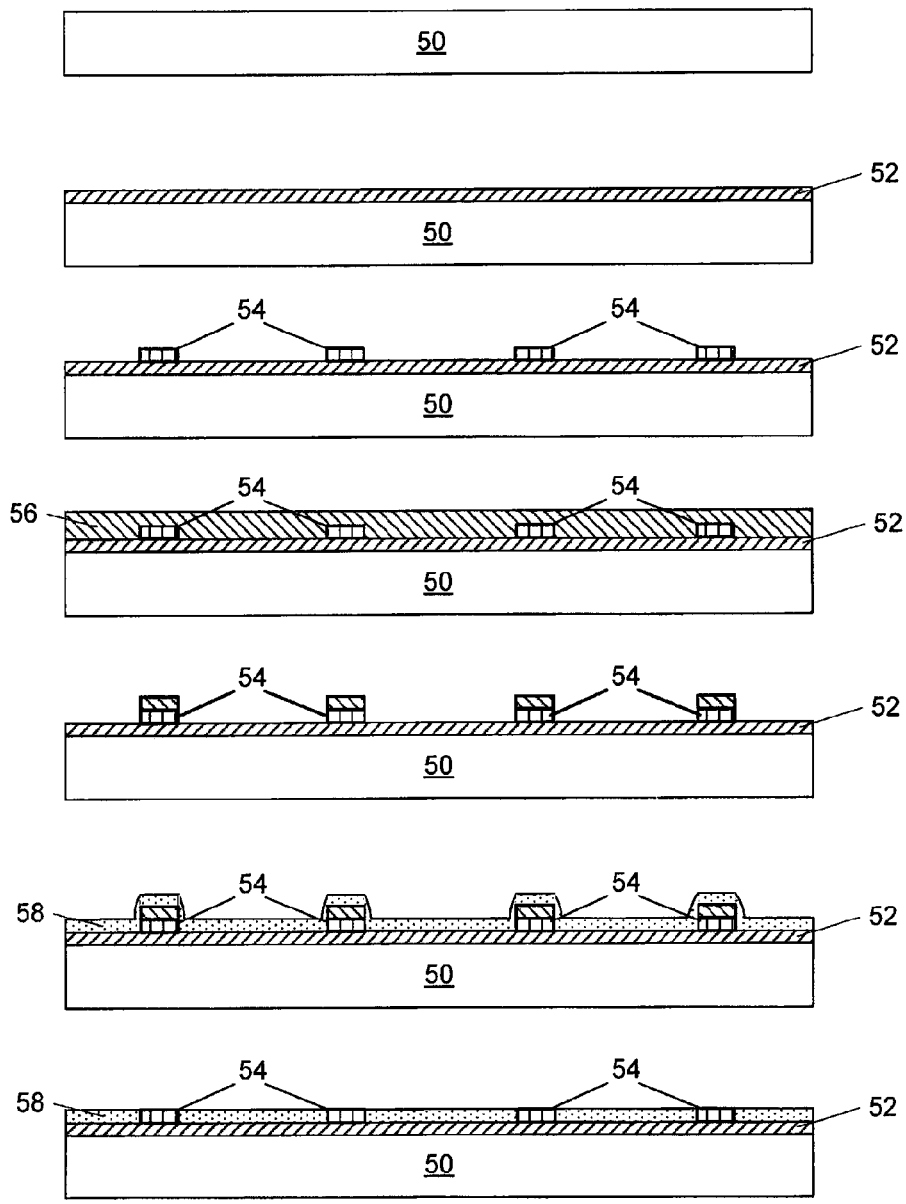
FIG. 5 depicts a fabrication process flow for an SPR assembly portion of a sample support such as that of FIG. 2.

The above-described procedure can also be used for the fabrication of the final top plate that contains nanopatterns (nanostuctures) to enhance the SPR signal so to obtain better sensitivity. In such an embodiment, the process starts with a pre-cleaned glass substrate 50, as shown in step (a) of FIG. 5. In step (b), an initial 20 nm layer of gold 52 is deposited. After this deposition, nanostructures are patterned using e-beam lithography in a polymethyl methacrylate (PMMA) resist, followed by 30 nm of gold deposition and liftoff to define the nanostructures 54 in the specific detection spots, as shown in step (c) of FIG. 5. A positive resist 56 is then spin-coated (step (d)), and patterned using photolithography (step (e)) to define the detection surface pattern. This selectively protects the detection spots regions from the subsequent hydrophobic coating 58, as shown in step (f). Finally, using a photoresist lift-off in acetone, the hydrophobic material is also removed from the detection spot regions, leaving the exposed gold nanostructures (step (g)).

Following the fabrication, the EWOD chip consisting of transparent (ITO-coated) top plate that can be tested using water droplet actuation in air surrounding medium to determine the required actuation voltage and the corresponding droplet transport speeds. Once determined, these parameters are then used with SPR biochips to transport the target ss-DNA to the specific detection spots onto which a complimentary ss-DNA probe has been immobilized. It should be noted that for biochips with surface patterning, higher voltage may be required to achieve the desired surface wettability.

The space between the plates can be adjusted to optimize displacement and sample deposition on the surface. In a preferred embodiment the space is between about 50 µm and 300 µm.

Testing of a chip according to the invention may be performed using a microscope and a CCD camera. The CCD camera may be mounted to the microscope objectives, positioned above the chip and used to assess and record the images of the droplet transport. The CCD camera can be connected to a monitor to allow a user to observe droplet displacement. A sample may be injected using a micropipette or a fluidic interconnect tubing. The composition of the droplet should also be optimized with respect to its polarity and sample compatibility such as to allow optimal displacement. Software protocols to design droplet transport routes are known. For instance U.S. Patent Application Publication Nos. US2006/021875 and US2006/036348 describe protocols and softwares to determine optimum droplet path to carry out a specific reaction on a microfluidic platform.

Bio-interface functionalization (binding of the sample to the surface) can be optimized using electronic addressing provided by the EWOD system to drive the sample to bare electrodes. Samples, such as DNA or proteins can be chemically derivatized to bind to the electrode surface. For example, thiol modified ss-DNA probes can be covalently attached to gold via sulfur-gold linkage. Careful control of the probe density is achieved by varying the amount of time that the gold electrode is exposed to the thiolated-DNA solution. Additionally, by applying an attractive electrostatic field at the interface, the efficiency of target capture can approach 100%, yielding a stronger detection signal. The use of selectively applied electric fields to deliver the target sample to the detection spots, besides reducing the sample consumption, also provides an enhancement in the intermolecular interaction dynamics and rate (such as DNA hybridization rates and dynamics), significantly reducing the assay time, and allowing for the real-time interaction detection using SPR imaging.

Bio-interface functionalization can be optimized as a function of the molecules involved. Attachment of molecules to surfaces for SPR detection is known in the art. For instance, U.S. Pat. No. 7,067,322 describes specific chemistry for immobilization of biomolecules to a metal substrate that involves depositing an omega-modified alkanethiol monolayer on substrate, UV photopatterning to create an array and contacting the monolayer with heterobifunctional linking compound via first moiety allowing the biomolecule immobilization. Another example is U.S. Pat. No. 5,629,213 that describes biomolecule attachment chemistry involving polylysine.

The system of the present invention can be used for studying molecular interactions such as DNA hybridization, antibody-antigen interactions, pathogen detection, bio-weapons identification and the like. The system can also be used as a tool for rapid detection.

The deposition of a sample (i.e., a target molecule) on the surface may be effected by guiding the droplet to the desired area and allowing sufficient time for the sample to be adsorbed onto the surface. Alternatively, in a situation where every "domain" of the surface is to be occupied by the same type of molecule, the surface can be simply incubated with the sample. Once the surface of the microfluidic sample support has been coated with the target molecule, the test molecule of interest is manipulated to be guided to the desired surface location and SPR measurements can be acquired. The system allows for either real time SPR signal acquisition or "static" signal acquisition in which the test molecule is allowed to reach equilibrium binding with the target molecule prior to signal acquisition.

Figure 6:
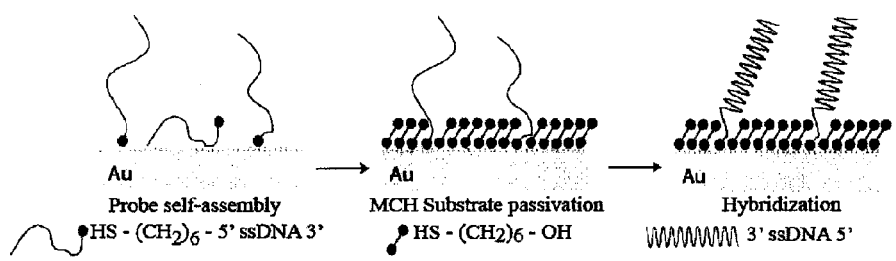
FIG. 6 is a schematic representation of DNA probe assembly on the surface of a sample support such as that of FIG. 2.

In one application of the invention, DNA (antibody pairs) can be modified to contain a thiolated end group that allows direct biomolecule attachment. Arraying onto the microfluidic sample support is achieved by transporting the droplet containing the thiolated biomolecule to the specific immobilization/detection spot on the upper plate of the device where the biomolecules will covalently attach to the metal surface (such as bare gold surface). As shown in the example of FIG. 6, thiol modified ss-DNA probes can covalently attach to gold via sulfur-gold linkage. DNA nucleotides can adsorb to gold via multiple amine moieties, as amines are known to chemisorb weakly to gold surfaces. Such adsorption at multiple sites can interfere with hybridization of the immobilized strands. As a remedy, the accessibility of immobilized probes to complementary target sequences can be enhanced by treating the surface with a small-molecule blocking agent, 6-mercapto-1-hexanol (MCH). The thiol group of MCH rapidly displaces the weaker adsorptive contacts between DNA nucleotides and the substrate, leaving the probes tethered primarily through the thiol end groups. After MCH treatment, the initially compact ss-DNA swells and extends further into solution. The less constrained tethering geometry renders the probes highly accessible to target, with nearly complete hybridization efficiencies. Instead of using molecules having the thiols directly incorporated into the ss-DNA backbone, an insulating carbon C6-linker may be used to prevent DNA base adsorption to gold surface and to retain the probe's biological activity.

Figure 7:
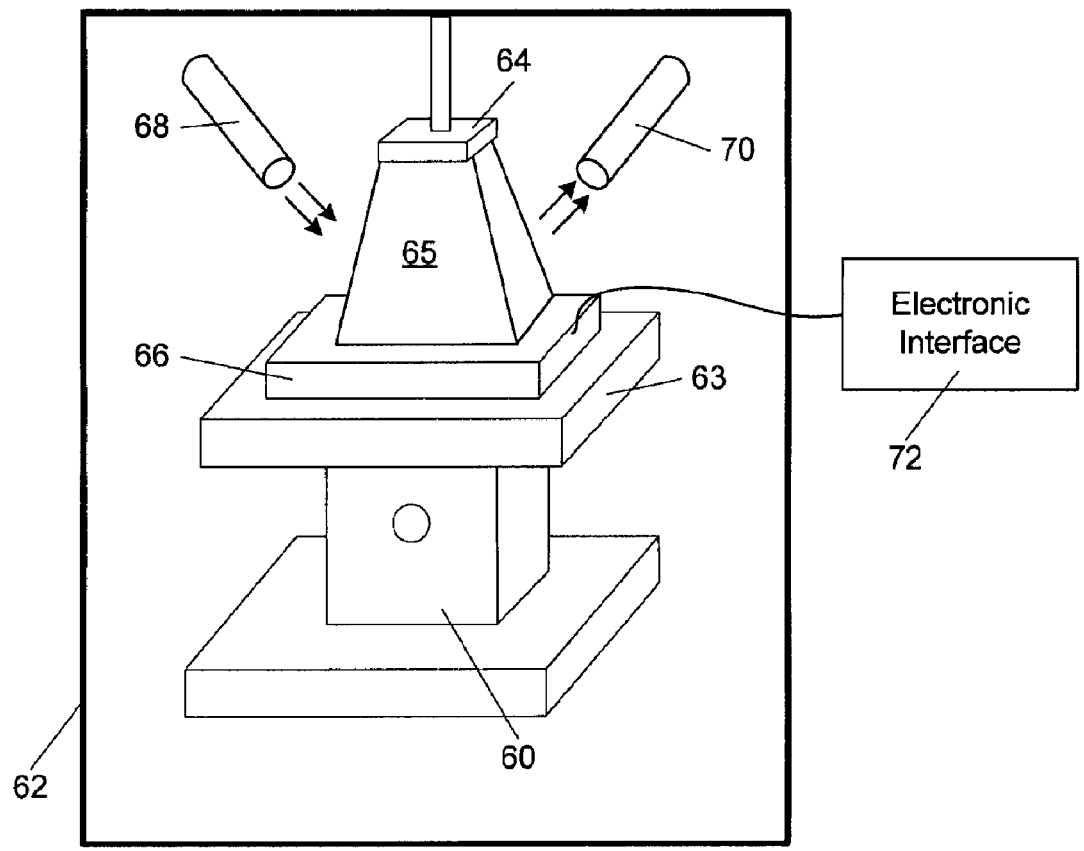
FIG. 7 is a schematic representation of a multichannel SPR detection arrangement using an SPR-EWOD sample support such as that of FIG. 2.

Some modifications to a conventional SPR apparatus may be carried out to accommodate an EWOD digital microfluidic platform as described herein. FIG. 7 shows a modified SPR-EWOD arrangement where an XYZ translation stage 60 supports a chip holder 63 that is attached to the translation stage 60 by screws (not shown). The chip 66 is, in turn, attached to the chip holder 63 by clips (not shown), or some other conventional means. Most of the components of the system are positioned inside a protective box 62, which serves as a shield from ambient light. An SPR prism 65 is connected to a prism holder 64, and may be positioned adjacent to the chip 66 by lowering it with a screw of the prism holder. This places it into contact with the top plate of the EWOD chip 66, to which it is optically coupled in the detection region by index-matching oil. Optical source 68 and CCD array detector 70, used for the SPR signal detection, are also shown in the figure. An electronic interface 72 is typically located outside of the box, and is connected to the system via a cable.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A method of manipulating a liquid droplet comprising:
providing a first plate comprising a predetermined pattern of independently addressable first electrodes on a surface of the first plate;
providing a second plate comprising a predetermined pattern of a continuous second electrode on a surface of the second plate, the predetermined pattern of the continuous second electrode having a first predetermined pattern of first nanostructures formed therein;
assembling the first plate and second plate in a predetermined orientation with respect to one another such that the predetermined pattern of independently addressable first electrodes and the first predetermined pattern of first nanostructures on the second electrode face one another and orientated relative to one another in a predetermined orientation determined in dependence upon the predetermined pattern of independently addressable first electrodes and the first predetermined pattern of first nanostructures on the second electrode;
providing a controller for generating a predetermined sequence of electrical signals to a predetermined subset of the predetermined pattern of independently addressable first electrodes in order to displace and position an isolated liquid droplet comprising a first liquid disposed between the first plate and second plate, the displacement and positioning of the isolated liquid droplet being made absent the presence of any other liquid between the first plate and second plate and absent any coating applied to the surface of the independently addressable first electrodes and the surface of the second electrode having the first predetermined pattern of first nanostructures.

2. The method according to claim 1 wherein,
the predetermined pattern of independently addressable first electrodes further comprises a second predetermined pattern of second nanostructures; and
the first predetermined pattern of first nanostructures and second predetermined pattern of second nanostructures provide an enhancement in displacing the isolated liquid droplet during its positioning and displacement by acting as hydrophobic elements in contact with the isolated liquid droplet.

3. The method according to claim 1 wherein,
a predetermined subset of the independently addressable first electrodes comprise a second predetermined pattern of second nanostructures;
predetermined regions of the continuous second electrode that are opposite the predetermined subset of the independently addressable first electrodes comprising a second redetermined pattern of second nanostructures comprise a third predetermined pattern of third nanostructures; and
the second predetermined pattern of second nanostructures and the third predetermined pattern of third nanostructures provide an enhancement in adhesion of the isolated liquid droplet during its positioning and displacement by acting as hydrophilic elements in contact with the isolated liquid droplet.

4. The method according to claim 1 wherein,
a predetermined subset of the independently addressable first electrodes comprise a second predetermined pattern of second nanostructures, the predetermined subset of the independently addressable electrodes being those that are not opposite a predetermined portion of the first predetermined pattern of first nanostructures on the second electrode;
the second predetermined pattern of second nanostructures provide an enhancement in displacing the isolated liquid droplet during its positioning and displacement by acting as hydrophobic elements in contact with the isolated liquid droplet; and
the first predetermined pattern of first nanostructures on the second electrode provide an enhancement in adhesion of the isolated liquid droplet during its positioning and displacement by acting as hydrophilic elements in contact with the isolated liquid droplet.

5. The method according to claim 1 wherein,
a predetermined region of the second continuous electrode absent the first predetermined pattern of first nanostructures is coated in a hydrophobic material; and the first nanostructures provide for an enhancement in the immobilization of the liquid droplet by acting as hydrophilic elements in contact with the isolated liquid droplet.

6. The method according to claim 1 wherein,
the first nanostructures provide for an enhancement in the electromagnetic field of an optical signal interacting with the isolated liquid droplet during surface plasmon resonance excitation.

7. The method according to claim 1 wherein,
a first predetermined portion of the isolated liquid droplet comprises an analyte and the composition of a second predetermined portion of the isolated liquid droplet is determined in dependence upon the analyte in order to enhance displacement of the isolated liquid droplet during its positioning and displacement.

8. A method of manipulating a liquid droplet comprising:
providing a first plate comprising a first predetermined pattern of independently addressable first electrodes on a surface of the first plate, a predetermined portion of the predetermined pattern of independently addressable first electrodes comprising a second predetermined pattern of first nanostructures formed therein;
providing a second plate comprising a hydrophobic material coated over a predetermined region of the second plate;
assembling the first plate and second plate in a predetermined orientation with respect to one another such that the predetermined pattern of independently addressable first electrodes and hydrophobic coating face one another and orientated relative to one another in a predetermined orientation determined in dependence upon the predetermined pattern of independently addressable first electrodes and the predetermined region of the second plate coated in a hydrophobic material; and
providing a controller for generating a predetermined sequence of electrical signals to a predetermined subset of the predetermined pattern of independently addressable first electrodes in order to displace and position an isolated liquid droplet comprising a first liquid disposed between the first plate and second plate, the displacement and positioning of the isolated liquid droplet being made absent the presence of any other liquid between the first plate and second plate and absent any coating applied to the surface of the independently addressable first electrodes and the surface of the second electrode having the first predetermined pattern of first nanostructures.

9. The method according to claim 8 wherein,
the predetermined pattern of independently addressable first electrodes further comprises a second predetermined pattern of second nanostructures;
the first predetermined pattern of first nanostructures provides an enhancement in displacing the isolated liquid droplet during its positioning and displacement by acting as hydrophobic elements in contact with the isolated liquid droplet; and
the second predetermined pattern of second nanostructures provides an enhancement in immobilizing the isolated liquid droplet during its positioning and displacement by acting as hydrophilic elements in contact with the isolated liquid droplet.

10. The method according to claim 8 wherein,
providing the hydrophobic material comprises providing a predetermined pattern of second nanostructures at least within one of the second plate and a material coating a predetermined portion of the second plate.

11. The method according to claim 8 further comprising;
providing a predetermined pattern of a predetermined binding agent on the first predetermined pattern of independently addressable first electrodes, the predetermined pattern defining detection locations within the first predetermined pattern of independently addressable first electrodes for a predetermined analyte, the predetermined binding agent being determined in dependence upon at least the predetermined analyte.

12. A device for manipulating a liquid droplet comprising;
a fluid handling system comprising:
providing a first plate comprising a predetermined pattern of independently addressable first electrodes on a surface of the first plate;
a second plate comprising a predetermined pattern of a continuous second electrode on a surface of the second plate, the predetermined pattern of the continuous second electrode having a first predetermined pattern of first nanostructures formed therein, the second plate positioned in a predetermined orientation with respect to one another such that the predetermined pattern of independently addressable first electrodes and the first predetermined pattern of first nanostructures on the second electrode face one another and orientated relative to one another in a predetermined orientation determined in dependence upon the predetermined pattern of independently addressable first electrodes and the first predetermined pattern of first nanostructures on the second electrode; wherein
a predetermined sequence of electrical signals applied to predetermined subsets of the predetermined pattern of independently addressable first electrodes to displace and position an isolated liquid droplet comprising a first liquid disposed between the first plate and second plate, the displacement and positioning of the isolated liquid droplet being made absent the presence of any other liquid between the first plate and second plate and absent any coating applied to the surface of the independently addressable first electrodes and the surface of the second electrode having the first predetermined pattern of first nanostructures;
a measurement system comprising:
an excitation source for coupling an electromagnetic wave of predetermined frequency to a predetermined region of the fluid handling system when disposed in predetermined relationship with the excitation source;
a measurement system for receiving a portion of the electromagnetic wave coupled to the predetermined region of the fluid handling system and determining at least one of a position and an intensity of the received portion of the electromagnetic wave, the portion being that reflected from the second electrode within the predetermined region of the fluid handling system;
a mounting system comprising:
a first mount for the fluid handling system; and
a second mount for the measurement system; wherein
the first mount allows for the insertion and removal of the fluid handling system and the mounting system provides for movement of the fluid handling system in and out of the predetermined relationship with the measurement system; and
a control system comprising at least a microprocessor for generating and applying the predetermined sequences of electrical signals to the predetermined subsets of the plurality of independently addressable first electrodes in order to displace and position the isolated liquid droplet for analysis using the measurement unit and determining a result in dependence upon at least one of the position and the intensity measured.

13. The device according to claim 12 wherein;
the predetermined pattern of independently addressable first electrodes further comprises a second predetermined pattern of second nanostructures; and
the first predetermined pattern of first nanostructures and second predetermined pattern of second nanostructures provide an enhancement in displacing the isolated liquid droplet during its positioning and displacement by acting as hydrophobic elements in contact with the isolated liquid droplet.

14. The device according to claim 12 wherein,
a predetermined subset of the independently addressable first electrodes comprise a second predetermined pattern of second nanostructures;
predetermined regions of the continuous second electrode that are opposite the predetermined subset of the independently addressable first electrodes comprising a second predetermined pattern of second nanostructures comprise a third predetermined pattern of third nanostructures; and
the second predetermined pattern of second nanostructures and the third predetermined pattern of third nanostructures provide an enhancement in adhesion of the isolated liquid droplet during its positioning and displacement by acting as hydrophilic elements in contact with the isolated liquid droplet.

15. The device according to claim 12 wherein,
a predetermined subset of the independently addressable first electrodes comprise a second redetermined pattern of second nanostructures, the predetermined subset of the independently addressable electrodes being those that are not opposite a predetermined portion of the first predetermined pattern of first nanostructures on the second electrode;
the second predetermined pattern of second nanostructures provide an enhancement in displacing the isolated liquid droplet during its positioning and displacement by acting as hydrophobic elements in contact with the isolated liquid droplet; and
the first predetermined pattern of first nanostructures on the second electrode provide an enhancement in adhesion of the isolated liquid droplet during its positioning and displacement by acting as hydrophilic elements in contact with the isolated liquid droplet.

16. The device according to claim 12 wherein,
the first nanostructures provide for an enhancement in the electromagnetic field of an optical signal interacting with the isolated liquid droplet during surface plasmon resonance excitation.

17. The device according to claim 12 wherein,
a first predetermined portion of the liquid droplet comprises an analyte and the composition of a second predetermined portion of the liquid droplet is determined in dependence upon the analyte in order to enhance displacement of the fluid droplet during its positioning and displacement.

18. A method of manipulating a liquid droplet comprising:
providing a fluid to a fluid handling system to provide a fluid droplet, the fluid handling system comprising:
providing a first plate comprising a predetermined pattern of independently addressable first electrodes on a surface of the first plate;
a second plate comprising a predetermined pattern of a continuous second electrode on a surface of the second plate, the predetermined pattern of the continuous second electrode having a first predetermined pattern of first nanostructures formed therein, the second plate positioned in a predetermined orientation with respect to one another such that the predetermined pattern of independently addressable first electrodes and the first predetermined pattern of first nanostructures on the second electrode face one another and orientated relative to one another in a predetermined orientation determined in dependence upon the predetermined pattern of independently addressable first electrodes and the first predetermined pattern of first nanostructures on the second electrode; wherein
a predetermined sequence of electrical signals applied to predetermined subsets of the predetermined pattern of independently addressable first electrodes displace and position an isolated liquid droplet comprising a first liquid disposed between the first plate and second plate, the displacement and positioning of the isolated liquid droplet being made absent the presence of any other liquid between the first plate and second plate and absent any coating applied to the surface of the independently addressable first electrodes and the surface of the second electrode having the first predetermined pattern of first nanostructures;
and
determining a characteristic of the isolated liquid droplet by providing the predetermined sequence of electrical signals to the first predetermined subset of the plurality of independently addressable first electrodes in order to displace and position the isolated liquid droplet to a predetermined location within the fluid handling system and performing a measurement based upon a surface plasmon resonance techniques such that the characteristic of the isolated liquid droplet is determined by at least one of angular and intensity based data obtained from the measurement.

19. The method according to claim 18 wherein the fluid handling system further comprises at least one of:
the predetermined pattern of independently addressable first electrodes further comprises a second predetermined pattern of second nanostructures; and
the first predetermined pattern of first nanostructures and second predetermined pattern of second nanostructures provide an enhancement in displacing the isolated liquid droplet during its positioning and displacement by acting as hydrophobic elements in contact with the isolated liquid droplet.

20. The method according to claim 19 wherein,
a predetermined subset of the independently addressable first electrodes comprise a second predetermined pattern of second nanostructures;
predetermined regions of the continuous second electrode that are opposite the predetermined subset of the independently addressable first electrodes comprising a second redetermined pattern of second nanostructures comprise a third predetermined pattern of third nanostructures; and
the second predetermined pattern of second nanostructures and the third predetermined pattern of third nanostructures provide an enhancement in adhesion of the isolated liquid droplet during its positioning and displacement by acting as hydrophilic elements in contact with the isolated liquid droplet.

21. A method of manipulating a liquid droplet comprising:
providing a first plate comprising a predetermined pattern of independently addressable first electrodes on a surface of the first plate and absent any coating applied to the surface of the independently addressable first electrodes;
providing a second plate comprising a predetermined pattern of a continuous second electrode on a surface of the second plate, the predetermined pattern of the continuous second electrode having a first predetermined pattern of first nanostructures formed therein providing an enhancement in displacing an isolated liquid droplet by acting as hydrophobic elements in contact with the isolated liquid droplet and a predetermined region comprising a second predetermined pattern of second nanostructures providing an enhancement in the electromagnetic field at the second electrode during surface plasmon resonance excitation and a third predetermined pattern of a predetermined binding agent relating to a predetermined analyte and absent any coating applied to the surface of the second electrode having the first and second nanostructures;
assembling the first plate and second plate in a predetermined orientation with respect to one another such that the predetermined pattern of independently addressable first electrodes and the first predetermined pattern of first nanostructures on the second electrode face one another and orientated relative to one another in a predetermined orientation determined in dependence upon the predetermined pattern of independently addressable first electrodes and the first predetermined pattern of first nanostructures on the second electrode; wherein
the isolated liquid droplet may be moved from a first location outside the predetermined region to a second location within the predetermined region by application of a predetermined sequence of electrical signals to a predetermined subset of the plurality of independently addressable first electrodes wherein the predetermined binding agent provides temporary binding of the analyte for a measurement to be performed by surface plasmon resonance excitation.

* * * * *